(12) United States Patent
Herweijer et al.

(10) Patent No.: US 10,531,981 B2
(45) Date of Patent: Jan. 14, 2020

(54) DEVICE FOR NON-SURGICAL COLD TREATMENT OF DISORDERS

(71) Applicant: YOUMEDICAL BRANDS B.V., Amsterdam (NL)

(72) Inventors: Jan Philip Herweijer, Amsterdam (NL); Robert Sebastiaan Stal, Amsterdam (NL); Johannes Hendricus Witte, Aerdenhout (NL); Job Kneppers, Den Hoorn (NL)

(73) Assignee: YOUMEDICAL B.V., Amsterdam (NL)

( * ) Notice: Subject to any disclaimer, the term of this patent is extended or adjusted under 35 U.S.C. 154(b) by 584 days.

(21) Appl. No.: 14/762,727

(22) PCT Filed: Jan. 23, 2014

(86) PCT No.: PCT/EP2014/051293
§ 371 (c)(1),
(2) Date: Jul. 22, 2015

(87) PCT Pub. No.: WO2014/114969
PCT Pub. Date: Jul. 31, 2014

(65) Prior Publication Data
US 2015/0359664 A1     Dec. 17, 2015

(30) Foreign Application Priority Data

Jan. 25, 2013  (EP) ..................................... 13152730
Jun. 10, 2013  (EP) ..................................... 13171281

(51) Int. Cl.
*A61M 35/00*     (2006.01)
*A61F 7/00*      (2006.01)
*A61B 18/02*     (2006.01)

(52) U.S. Cl.
CPC ............ *A61F 7/0085* (2013.01); *A61B 18/02* (2013.01); *A61B 18/0218* (2013.01);
(Continued)

(58) Field of Classification Search
CPC ............ A61F 7/0085; A61F 2007/0052; A61F 2007/0056; A61F 2007/0087;
(Continued)

(56) References Cited

U.S. PATENT DOCUMENTS 3,768,703 A * 10/1973 Markowitz ............ B65D 83/40
                                                    222/182
4,345,598 A    8/1982 Zobac et al.
(Continued)

FOREIGN PATENT DOCUMENTS

EP    1929981    6/2008
GB    2079608    1/1982
(Continued)

OTHER PUBLICATIONS

International Search Report and Written Opinion from corresponding foreign application PCT/EP2014/051293, filed Jan. 23, 2014.

*Primary Examiner* — Adam Marcetich
*Assistant Examiner* — Jessica R Arble
(74) *Attorney, Agent, or Firm* — Steven M. Koehler; Westman, Champlin, Koehler, P.A.

(57) ABSTRACT

A device for non-surgical cold treatment of disorders, like warts includes a container containing a refrigerant having an outlet and a valve communicating with the outlet. An applicator is mounted to the container, said applicator having an outer wall and forming a chamber at least when connected to the container, a heat exchanger within the chamber in fluid communication with the outlet of the container and receiving refrigerant when the valve of the container is opened. A closed contact member is in heat exchange contact with the heat exchanger and is exposed to an outer side of the applicator. The heat exchanger includes a porous member made of a material having a high thermal conductivity and adapted to conduct fluid refrigerant from the outlet of the container to the chamber while the refrigerant extracts heat from the heat exchanger and the contact member.

23 Claims, 5 Drawing Sheets

(52) U.S. Cl.
CPC ... *A61M 35/003* (2013.01); *A61F 2007/0052* (2013.01); *A61F 2007/0056* (2013.01); *A61F 2007/0087* (2013.01)

(58) Field of Classification Search
CPC ............... A61B 18/02; A61B 18/0218; A61B 2018/0275; A61B 2018/00011; A61M 35/003; B65D 83/222; B65D 83/226; B65D 2215/00; B65D 2215/02; B65D 2215/04; B65D 83/40; B65D 83/205; B65D 83/207
See application file for complete search history.

(56) References Cited

U.S. PATENT DOCUMENTS

| | | | | |
|---|---|---|---|---|
| 6,126,044 | A | * | 10/2000 | Smith ............... B65D 83/206 222/1 |
| 8,906,005 | B2 | * | 12/2014 | Formica ............ A61B 18/0218 606/25 |
| 2008/0142036 | A1 | * | 6/2008 | Sanchez ............... A45D 34/04 132/320 |
| 2008/0210710 | A1 | * | 9/2008 | Marquardt ........... B65D 83/206 222/153.11 |
| 2011/0152851 | A1 | * | 6/2011 | Formica ............ A61B 18/0218 606/25 |
| 2012/0277696 | A1 | * | 11/2012 | Gonzalez-Zugasti ....................... A61B 5/1411 604/318 |
| 2015/0313662 | A1 | * | 11/2015 | Ottanelli ............ A61B 18/0218 606/25 |

FOREIGN PATENT DOCUMENTS

| | | | | |
|---|---|---|---|---|
| GB | 2079608 | A | * 1/1982 | ............. A61B 18/02 |
| GB | 2079608 | A | * 1/1982 | ............. A61B 18/02 |

* cited by examiner

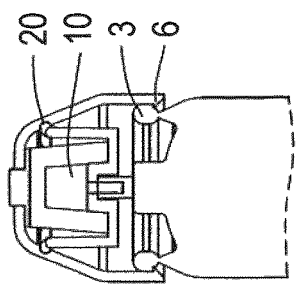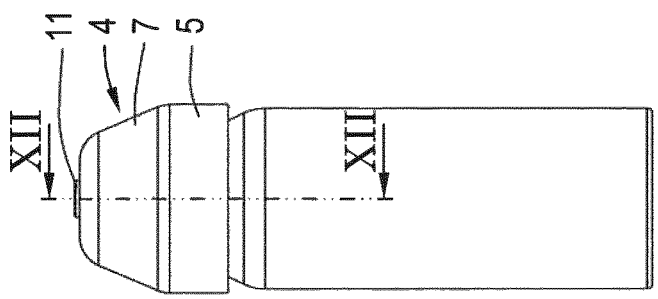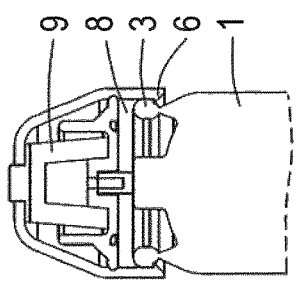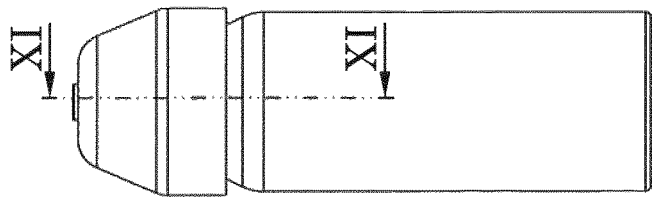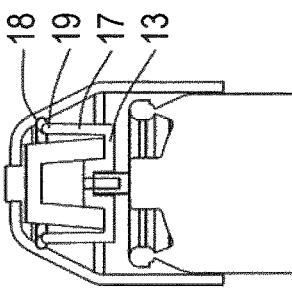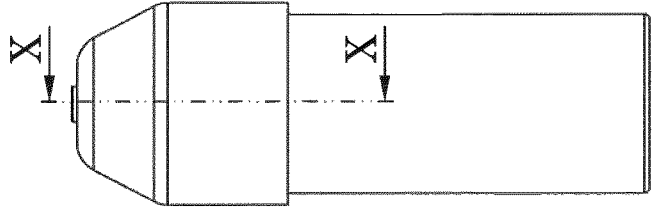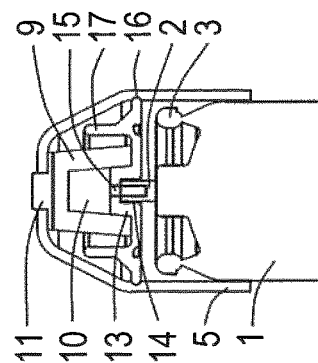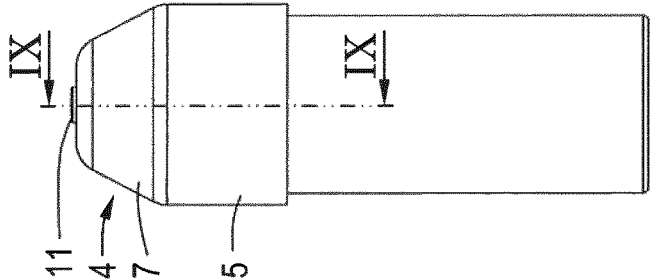

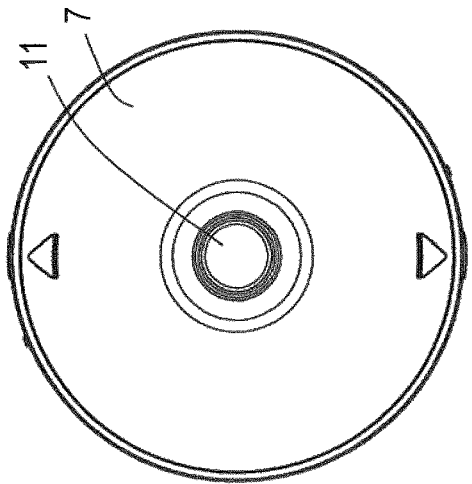
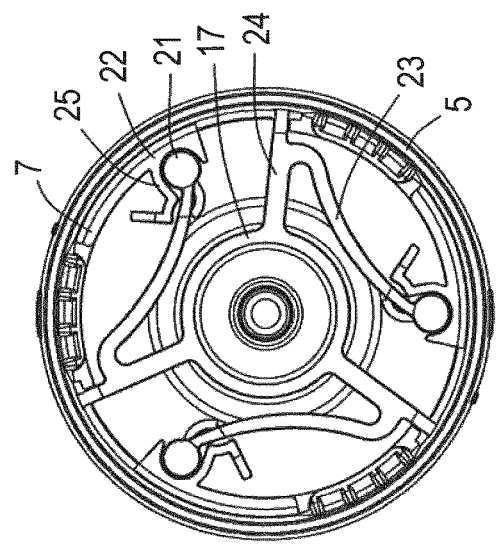
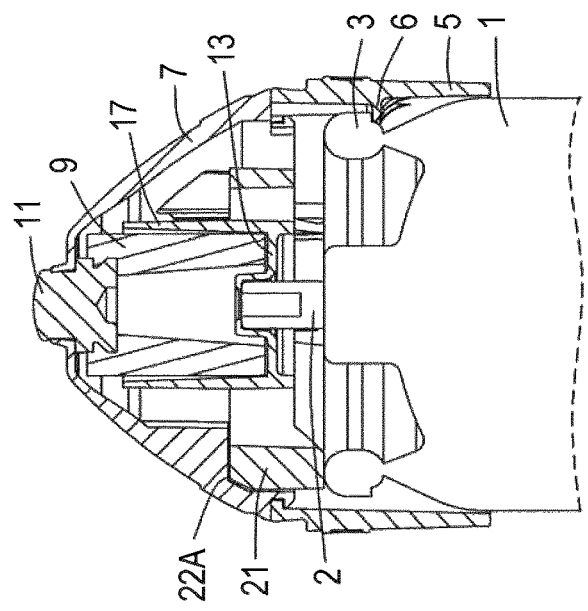
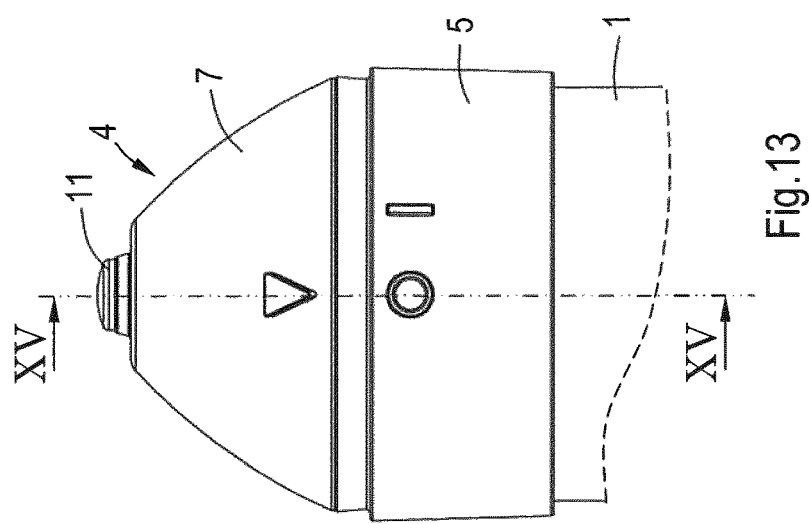

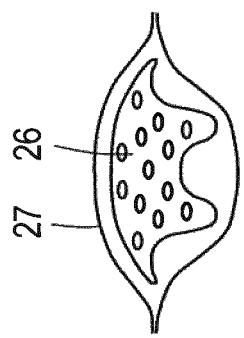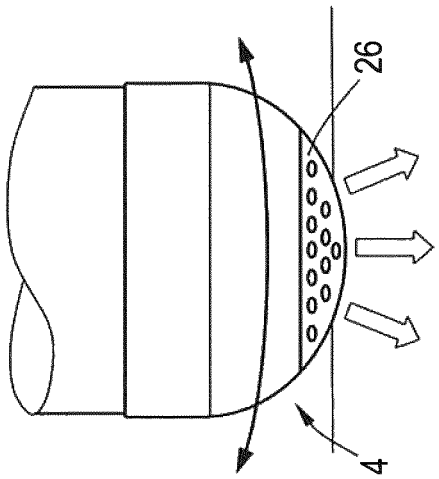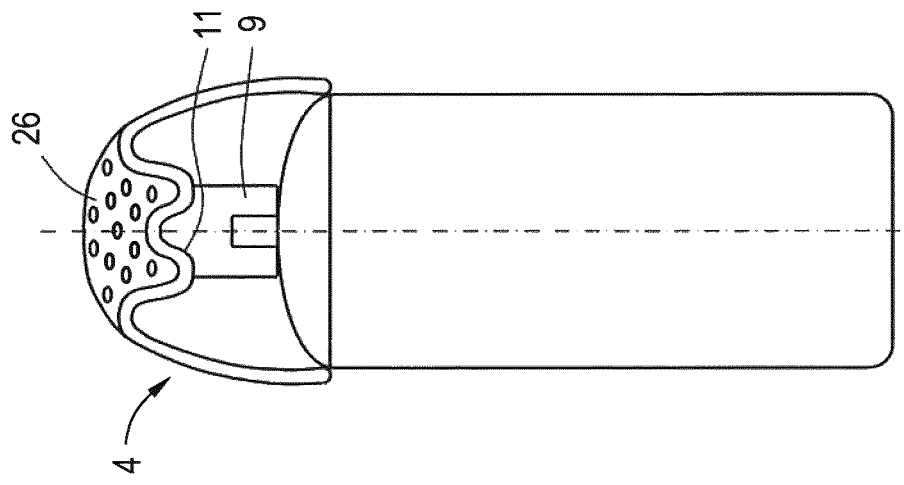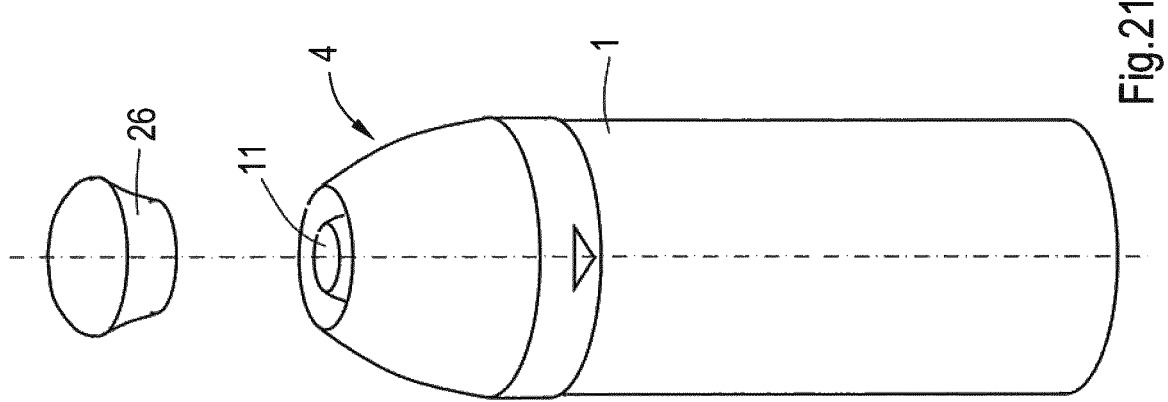

DEVICE FOR NON-SURGICAL COLD TREATMENT OF DISORDERS

CROSS-REFERENCE TO RELATED APPLICATION

This application is a Section 371 National Stage Application of International Application PCT/EP2014/051293 filed Jan. 23, 2014 and published as WO 2014/114696 A1 in English.

BACKGROUND

The discussion below is merely provided for general background information and is not intended to be used as an aid in determining the scope of the claimed subject matter.

The invention relates to a device for non-surgical cold treatment of disorders, comprising a container containing a refrigerant and having an outlet for the refrigerant and a valve communicating with the outlet, and an applicator mounted or mountable to the container, said applicator having an outer wall and forming a chamber at least when connected to the container.

Such devices are known from the prior art but most of them have not yet led to a successful use in practice. The devices that have reached commercial stage, which are mainly meant for the treatment of warts, are all open systems in which the refrigerant is supplied to the site to be treated. The refrigerant directly cools this site. The disadvantage of these devices is that the treatment is hardly controllable. The type of refrigerant determines the temperature and the cooling time is mainly determined by the refrigerant that is supplied to the site which is difficult to control. There is also a risk that the refrigerant damages or affects more skin than necessary for the treatment if refrigerant is spilled or supplied to the wrong place.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background The present invention has as one of its objects to provide a novel device that is more practical in use.

The device comprises a heat exchanger within the chamber in fluid communication with the outlet of the container and receiving refrigerant when the valve of the container is opened, a closed contact member in heat exchange contact with the heat exchanger and being exposed to an outer side of the applicator, wherein the heat exchanger comprises a porous member made of a material having a high thermal conductivity and adapted to conduct fluid refrigerant from the outlet of the container to the chamber while the refrigerant extracts heat from the heat exchanger and the contact member.

The porous heat exchanger can provide a very efficient exchange of cooling energy from the refrigerant to the contact member. Since the contact member is closed, refrigerant cannot arrive at the site to be treated, only cooling energy can reach this site. A control of the minimum temperature and the duration of the low temperature can be obtained if desired, for example by controlling the amount of refrigerant supplied to the heat exchanger or by the design of the heat exchanger. The shape of an outer surface of the contact member can easily be varied and adapted to the disorder to be treated, so that the device as a whole may be designed specifically for a wide range of disorders.

For low temperature cost effective heat exchangers (for example reaching temperatures of −10° C. to −50° C.), it is favorable to use a sintered metal for the porous member, for example sintered brass, although other metals having good heat conducting properties are conceivable, such as aluminium, copper, steel etc. For applications using higher temperatures, for example in the range from −10° C. to +10° C. it is also possible to make the heat exchanger partly or wholly from porous plastic.

To further improve the efficiency of the heat exchanger, the conductive porous member may at least partly be surrounded by a receptacle to receive any liquid refrigerant from the porous member therein, the receptacle being open to or vented to the chamber.

By receiving the refrigerant escaping from the porous member and keeping it close to the heat exchanger, the refrigerant will still cool the porous member even though it has left the porous member. If the receptacle and the porous member form a narrow space between them, the refrigerant will even be spread over the outer surface of the porous member to enhance transfer of cooling energy.

The receptacle may be directly attached to the applicator, in particular to the outer wall thereof, for example by a snap connection. This is a simple way of attaching the receptacle and possibly also the heat exchanger to the applicator.

In order to prevent liquid refrigerant to leave the applicator in case the applicator forms a chamber together with the container, the applicator connects to the container so as to hold fluid therein but to allow gas to escape. A slidable close contact between the applicator and the container may be sufficient for reaching this goal. Such slidable contact is also useful if the applicator is at least slidable in axial direction with respect to the substantially cylindrical container in order to actuate the valve of the container.

In one embodiment, the applicator is provided with a child-proof lock to prevent unwanted actuation of the device. For example, if the applicator has a member in contact with the outlet of the container which is surrounded by a collar, and if an axial movement of the member causes axial depression of the outlet of the container to open the valve thereof, then the child-proof lock may be positioned within the outer wall of the applicator and include at least one locking member which is movable between a locking position axially in line with the collar of the container to prevent a relative axial movement of the applicator and an unlocking position in which it is displaced radially inwardly of the collar allowing a relative axial movement of the applicator, a transmitting member being arranged between the outer wall and the at least one locking member to convert a non-axial movement of the outer wall into a movement of the at least one locking member from the locking position to the unlocking position.

In another embodiment the device is provided with a cover for the applicator covering the contact member. This especially useful if the device is actuated by depressing the applicator with respect to the container. This can then be done when the cover is on the applicator, avoiding the risk of touching the cold contact member during actuation.

The contact member protruding through the outer wall of the applicator and the heat exchanger fixed thereto may be sealed with respect to the outer wall at an inner surface thereof. Due to the temperature differences in the device (and the resulting dimensional changes in the heat exchanger), it is easier to obtain a seal in axial direction than in radial direction, for example by allowing the heat exchanger to be in pressing contact with the inner surface of the outer wall of the applicator.

The applicator can be made removable from the container, the applicator having a substantially cylindrical sleeve portion which is slidably guided on the outer surface of the container, but allowing the applicator to slide off of the container. If the applicator is not removable, the sleeve can be shorter, but there will be a stop preventing removal.

In one embodiment, the substantially cylindrical contact member slightly protrudes through the outer wall of the applicator and terminates in a substantially circular shaped skin contact surface, and the outer wall of the applicator may substantially have the shape of a dome extending concentrically around the contact member.

The invention also relates to a method of operating a device for the cold treatment of disorders. It comprising the steps of providing a device having a container containing a refrigerant and including an outlet with a valve actuated by pressing, an applicator mounted on the container and connected to the outlet, a contact member mounted in and protruding from the applicator, and preferably a cover removably mounted on the applicator, depressing the cover or applicator to actuate the valve through the applicator, waiting until the temperature of the contact member has reached the right temperature and removing the cover from the applicator, if applicable, applying the contact member of the applicator to the disorder.

BRIEF DESCRIPTION OF THE DRAWINGS

Further details and advantages of the invention will follow from the following description with reference to the accompanying drawings showing exemplary embodiments of the invention.

FIGS. 5-8 are side views of the devices shown in FIGS. 1-4.

FIGS. 9-12 are sectional views according to the lines IX-IX, X-X, XI-XI and XII-XII in FIGS. 5-8.

FIG. 13 is a partial side view of a further embodiment of the device in its position locked against actuation.

FIG. 14 is a plan view of the device of FIG. 13.

FIG. 15 is a sectional view according to the line XV-XV in FIG. 13.

FIG. 16 is a bottom view of the applicator without the container.

FIG. 21 is a schematic perspective view of a further embodiment of the device in which a separate porous member containing an active ingredient is used.

FIG. 22 is a very schematic, partially cut-away side view of the device of FIG. 21 with the porous member attached.

FIG. 23 is an illustration of the use of the device of FIGS. 21 and 22.

FIG. 24 is a schematic side view of the separate porous member within a packaging before use.

DETAILED DESCRIPTION OF THE ILLUSTRATIVE EMBODIMENTS

Figure 4:
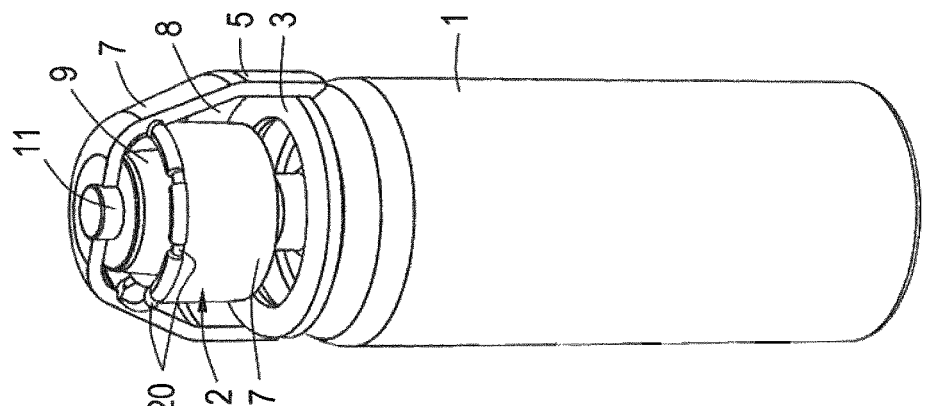
FIGS. 1-4 are perspective views, partially broken away, showing 4 different embodiments of the device of the invention.

The drawings show several embodiments of a device for the cold treatment of human body disorders, in particular skin disorders like warts, age spots, skin tags, burns, insect bites, rings or bags under the eyes, bruises or swellings, but also disorders in external body cavities like nose, ear, mouth and also for example piles in the anus. These disorders can be treated non-surgically by supplying cooling energy to the site, i.e. epicutaneous. This can be done by a physician or by the patient him/herself. In some applications, for example with warts, the temperature of the device should be very low, in the order of −30° C. to −50° C., in order to freeze the disorder. In other applications, for example with swellings or cosmetic applications, the temperature can be much higher, around 0° C.

The devices shown in the drawings are all intended for treating warts with deep freezing temperatures.

The device includes a container 1 containing a refrigerant. The refrigerant can be selected depending on the particular application of the device and the required temperatures. In this case it is an aerosol containing butane/propane, but can also be liquefied $CO_2$ or any other useful refrigerant. Refrigerant is to mean any liquid or gas which is able to extract heat due to evaporation and/or expansion or other cooling processes. So, for example, also propellants that have a cooling effect are considered to be a refrigerant. The container may be a standard spray or aerosol can having a valve (not shown) and an outlet tube 2 (see FIGS. 9-12). The can may have a capacity of 25-250 ml, more particular 50-100 ml, for example. The container 1 is more or less cylindrical having a collar 3 spaced around the outlet tube 2.

An applicator 4 is mounted on container 1 at the end containing outlet tube 2. For this mounting purpose, applicator 4 comprises a sleeve portion 5 adapted to engage around the outer surface of container 1.

Figure 2:
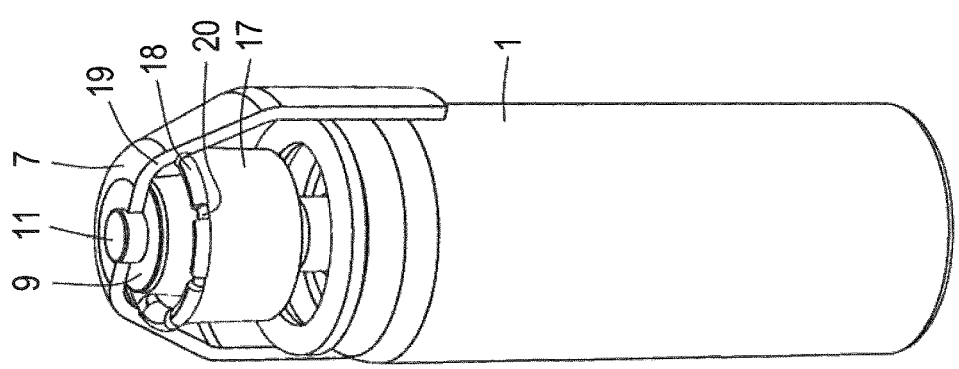
Figure 1:
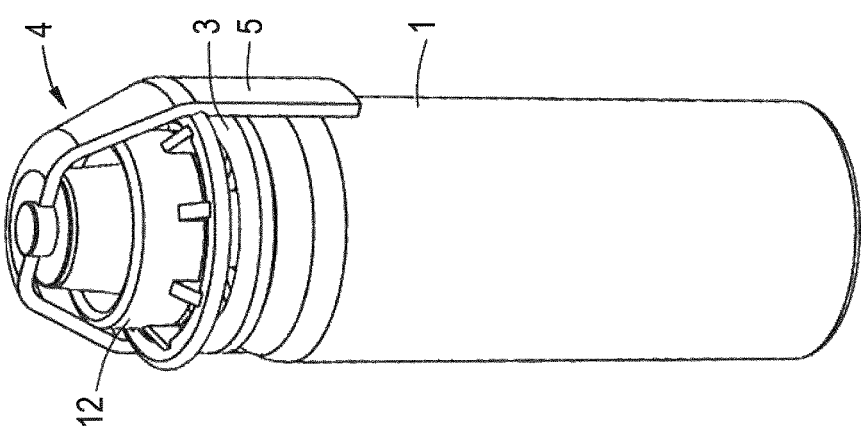
Figure 18:
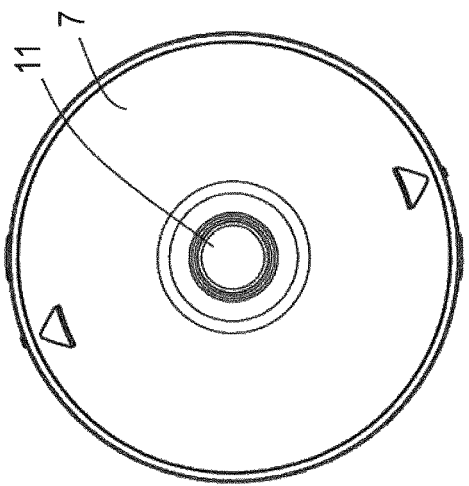
FIGS. 17-20 are views corresponding to those of FIGS. 13-16, but showing the applicator in the unlocked position, in which it may be actuated.
Figure 20:
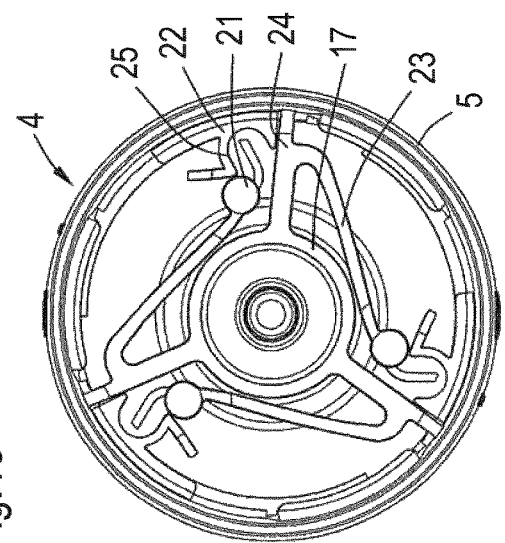
Figure 19:
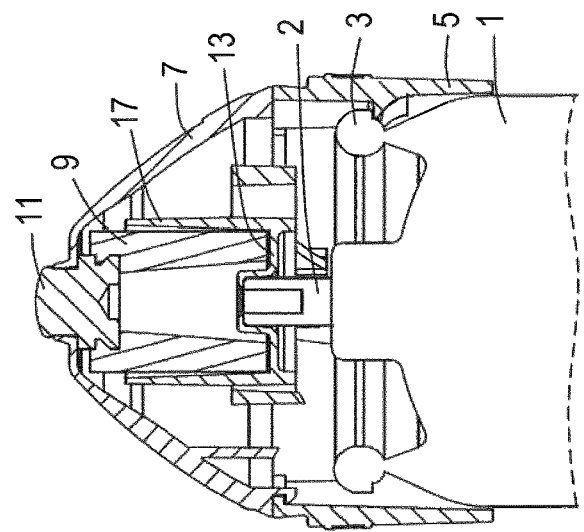
Figure 17:
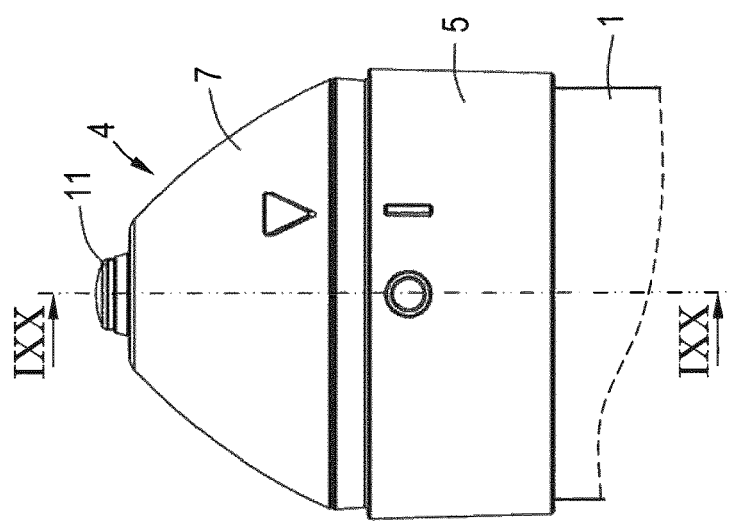

In the embodiments of FIGS. 1 and 2, sleeve portion 5 is relatively long and engages around a considerable length of container 1, at least up to the cylindrical main portion of the container. In this embodiment, applicator 4 is removable from container 1. The sleeve portion 5 is just engaging around container 1 with a sliding (frictional) fit and without any stop preventing removal of applicator 4.

Figure 3:
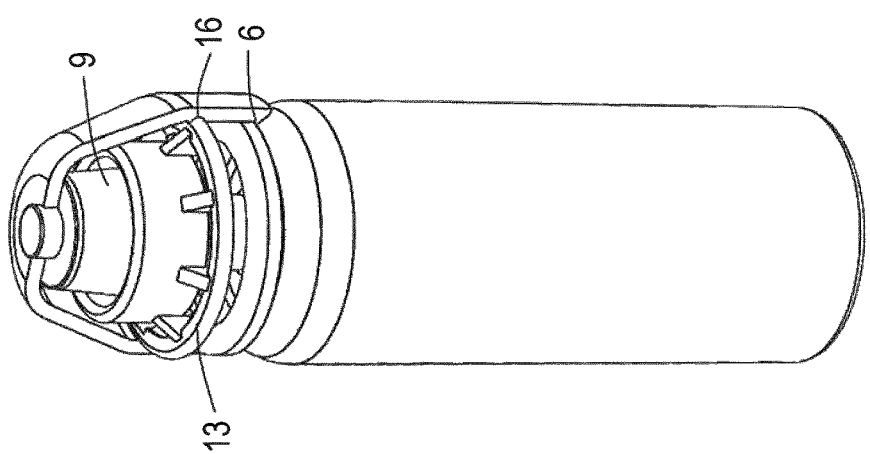

In the embodiment of FIGS. 3 and 4, sleeve portion 5 is shorter, but comprises an inner ridge 6 or the like at the open end of sleeve portion 5 engaging behind collar 3 of container 1, thus functioning as a stop preventing removal of applicator 4 and determining the non-actuating position of the applicator on the outlet tube 2 and valve.

In both embodiments, the valve of container 1 is actuated by depressing outlet tube 2 by means of applicator 4 which must thus also be depressed. During this sliding movement, the applicator is guided by sleeve portion 2 engaging around container 1 and by outlet tube 2.

The sleeve portion 5 of applicator 4 is part of an outer wall thereof and connects to a dome-shaped wall portion 7. These wall portions 7 together with the top of container 1 define a chamber 8 within applicator 4. The sleeve portion 5 may be sealed to container 1 in such a way that it prevents leakage of liquid refrigerant from chamber 8, but allows the passage of gaseous refrigerant.

Mounted within chamber 8 is a heat exchanger comprising a porous member 9, for example made from a material having good heat conducting properties. One example thereof is sintered metal such as brass having pores allowing passage of refrigerant. The porous member 9 is positioned around the outlet opening of outlet tube 2 of container 1. The porous member 9 has a cavity 10 (see FIGS. 9-12) where the refrigerant from outlet tube 2 enters and where it will expand thereby absorbing energy from the cavity and surrounding porous member 9 thus effecting a cooling thereof. On the end of porous member 9 remote from outlet tube 2 and adjacent the wall portion of applicator 4, there is provided a contact member 11 to contact the site to be treated. This contact member and/or the heat exchanger is closed such that refrigerant cannot escape from the heat exchanger or chamber 8 through this contact member 11. This contact member 11 can be a separate part attached to porous member 9, but it may also be integrated in the porous member, while it is made impermeable, for example by melting, impregnating or adding a separate part or layer of metal or plastic to porous member 9. The contact member 11 is mainly cylindrical and slightly protrudes through an opening in the top of the dome-shaped wall portion 7 of applicator 4, which is flattened in the embodiment shown, so that wall portion 7 is substantially in the form of a truncated cone, having in its center the circular outer surface of contact member 11. However, contact member 11 may be covered by a thin protective layer of for example plastic in some embodiments. The contact member does not have to protrude completely through the outer wall of applicator 4. It just needs to be exposed to such an extent that it can cool the site to be treated to a desired extent, either directly, or indirectly through an additional member.

The porous member 9 is mounted within applicator 4 by means of a mounting member 12. This mounting member 12 is here formed as a separate plastic part. It has a bottom portion 13 including in its center a cavity 14 in which outlet tube 2 fits. Cavity 14 communicates with a passage 15 through bottom portion 13 to allow refrigerant to enter cavity 10 within porous member 9 through bottom portion 13 of mounting member 12.

In the embodiments of FIGS. 1 and 3, bottom portion 13 extends up to the outer wall of applicator 4, in particular sleeve portion 5 thereof. This is provided with a circumferential inner groove 16 in which the circumferential edge of bottom portion 13 can snap to attach the mounting member 12 to the outer wall of applicator 4 and thereby also mounting porous member 9 and contact member 11. In fact, when mounting member 12 is seated with its edge in groove 16 it presses porous member 9 against the outer wall of applicator 4 surrounding the opening for contact member 11. This pressing contact enables a gas tight seal (with or without any assistance of a sealant) between the upper surface of porous member 9 and the inner surface of outer wall portion 7 of applicator 4 thus preventing escape of refrigerant there, also with varying temperatures of porous member 9 due to the refrigerant.

The mounting member 12 in the embodiments of FIGS. 1 and 3 includes an upright wall member 17 forming together with bottom portion 13 a receptacle for any liquid refrigerant escaping from porous member 9. The wall member ends at a distance from the outer wall of applicator 4, so that receptacle is open to chamber 8 of the applicator. The wall member 17 closely surrounds the outer surface of porous member 9 thus only leaving a narrow annular space between them thereby forcing any liquid refrigerant to stay in contact with the outer surface of porous member 9 and thus withdrawing heat from porous member 9. This improves the efficiency of the heat exchanger.

When during normal use of the device the valve of the container is actuated with the device in an upright position, all liquid refrigerant will be received in the receptacle and will be evaporated before the applicator is moved to an upside down position in which contact member 11 is exposed to the site to be treated. The bottom portion 13 outside upright wall member 17 will normally be open to allow gaseous refrigerant to escape.

In the embodiments of FIGS. 2 and 4, mounting member 12 is formed differently. Bottom portion 13 is now terminated short of sleeve portion 5, but upright wall member 17 is extended up to inner surface of dome shaped wall portion 7 and the upper end of wall member 17 is provided with a collar 18 adapted to snap into a groove 19 in the inner surface of outer wall portion 7. In order to vent the receptacle to chamber 8 of the applicator, one or more recesses 20 or openings are provided in collar 18 (see FIGS. 2 and 4) so that gaseous refrigerant can escape from the receptacle to chamber 8 and then to the environment.

Not shown in the drawings is a cover that fits onto the applicator to cover the contact member. The cover or the applicator may be provided with a child lock, for example such that the cover and applicator can only be depressed after a small rotation of the cover and/or applicator. This can be effected by providing a member allowing depression of the applicator in one rotational position and preventing depression in another rotational position.

Use of the devices as shown is as follows. In the unlocked position, applicator 4 is depressed with respect to container 1 against spring pressure of the valve, preferably with the cover on the applicator. Depressing is continued until a sufficient amount of refrigerant from container 1 has entered cavity 10 within porous member 9 of the heat exchanger. There the liquid refrigerant will evaporate and withdraw heat from the porous member so that the temperature thereof will drop. The pores of the porous member 9 will enable a good and wide spread contact between the refrigerant and the material of porous member 9. Due to the good heat conducting properties, also the temperature of contact member 11 will drop to the same degree, depending on the type of and amount of refrigerant supplied to the heat exchanger. Any liquid refrigerant that passes through the porous member will be received in the receptacle formed by bottom portion 13 and upright wall member 17 and thus is kept in close contact with the heat exchanger. If the pressure in chamber 8 is rising above that of the environment, gaseous refrigerant may escape between the sleeve portion 5 and outer surface of container 1. Due to the pressure between the upper surface of porous member 9 and the lower surface of outer wall portion 7 exerted by mounting member 12 and by the user depressing the applicator, no gaseous refrigerant will escape at the position of contact member 11.

After a prescribed time, the temperature of contact member 11 will be at the required level and the user may stop depressing applicator 4 so that it will return to its rest position by the spring force of the valve of container 1. The user may remove the cover, if he/she has not already done so. The contact member 11 may then be brought into contact with the site to be treated, for example with the wart. The wart will be frozen by the contact member and due to the limited surface that is at such lowered temperature, there is no risk of surroundings of the wart being frozen, so that there is hardly any risk of skin burns. In this application, the upper surface of the contact member may for example be between 3 and 5 mm, in particular substantially 4 mm.

In the embodiment of FIGS. 1 and 2, the applicator may or may not be removed from the container before it is applied to the site to be treated.

FIGS. 13-16 show a further embodiment of the applicator, which is provided with a child-proof lock to prevent the applicator from becoming activated, in this case depressed, by a child. In this embodiment, the housing of the applicator is made in two parts: sleeve portion 5 is mounted on container 1 and dome-shaped outer wall portion 7 is mounted to sleeve portion 5, such that wall portion 7 is axially fixed but may rotate to a limited extent with respect to portion 5, around an axis which is in line with the axis of container 1. The sleeve portion 5 shows in opposite positions two markings: an O indicating the rotational position of dome-shaped portion 7 in which the activation is disabled (a marking ▼ on dome-shaped wall portion 7 is then aligned with the O), and an I with which the marking ▼ must be aligned in order to be able to activate the applicator by jointly depressing dome-shaped wall portion 7 and sleeve portion 5. The two markings may be off-set e.g. 10-30°, such as ca. 22°.

In this embodiment, dome-shaped wall portion 7 is biased towards its disabled position, so that a user must hold the dome-shaped wall portion 7 in its rotated position when it is depressed. When the user releases dome-shaped wall portion 7 it will spring back to its locked position.

The child-proof lock in this embodiment comprises locking members in the form of locking cams 21. In the locking position, these cams 21 are positioned in seats 22 near the circumference of wall portion 7. The cams 21 are then positioned above upper collar 3 of container 1, thereby preventing a downward movement of dome-shaped portion 7 and sleeve portion 5 because cams 21 are stopped by collar 3. Each seat 22 includes a supporting surface 22A supporting the respective cam 21 in axial direction. The cams 21 are mounted at free ends of transmitting or holding members, here flexible arms 23 which are curved and which are mounted on their ends remote from cams 21 to a part of the applicator that is connected to sleeve portion 5, in this case to radial ribs 24 extending between upright wall member 17 and sleeve portion 5. The arms 23 extend mainly in circumferential direction and connect to cams 21 more in radial direction.

The seats 22 have a seat wall portion 25 mainly in radial direction on the side of arms 23. These seat wall portions 25 urge cams 21 radially inwardly when the seats 22 are moved mainly in circumferential direction upon rotation of dome-shaped wall portion 7 and the arms 23 are held by ribs 24 thereby pulling cams 21 away from their seats 24 to move along the seat wall portions 25. This inward, more or less radial movement of cams 21 causes cams 21 to move out of engagement with collar 3, such that there is no part below cams 21 blocking their movement. The cams and therewith dome-shaped wall portion 7 and sleeve portion 5 may then be depressed with respect to container 1. As a result, outlet tube 2 of container 1 may be depressed by a member of applicator 4, in this case bottom portion 13 of mounting member 12, and thus the valve of the container is opened to allow coolant to enter applicator 4. When dome-shaped wall portion 7 is released, it will spring back upwardly by the spring pressure of outlet tube 2, while the spring pressure in arms 23 will rotate dome-shaped wall portion 7 back to the locked position with the cams aligned with collar 3 of the container 1.

In an alternative embodiment not shown, the spring force of the arms may be reduced such that dome-shaped wall portion 7 will not be biased to the locked position. The dome-shaped wall portion 7 may then remain in the unlocked position (aligned with I) and may be rotated back to the locked position manually. In such embodiment, wall portion 7 and sleeve portion 5 may be provided with click members to mark the locked and unlocked position. It is conceivable to connect the holding and locking members to the dome-shaped outer wall portion 7 and to form the seats to the sleeve portion 5, as long as there is a relative movement between the locking members and a part moving the locking member(s) away from the collar of the container.

The movement of the locking member(s) away from the collar could also be outwardly, or axially away from the collar. If the sleeve portion 5 would be axially stationary with respect to the container, and wall portion 7 would be axially movable with respect to the sleeve portion, then the locking members could also cooperate indirectly with the collar through a part of sleeve portion 5.

The child-proof lock can be used with other devices as well, where an aerosol can is activated to release a substance by depression of an applicator (which may also be a spraying device or the like).

From the foregoing it will be clear that the invention provides a device which is very easy to handle and operate without the risk of skin burns. The device can be easily controlled either by design and/or operation. For example, temperature can be controlled either by the choice of material for the heat exchanger/contact member or by regulating the amount of refrigerant supplied. This can be done either manually or automatically by for example a time switch or bimetal switch in the supply.

The invention is not limited to the embodiments shown in the drawings and described above which can be varied in different manners within the scope of the invention. First of all, it is noted that features of different embodiments can be used in other combinations. Furthermore, it is possible to replace parts of the device by alternative arrangements. For example, in stead of a sintered porous member, it is possible to use a member having one or more channels or passages formed therein allowing close contact between refrigerant and heat exchanger. The receptacle to keep escaping liquid refrigerant in close contact with the heat exchanger can be combined with different types of heat exchangers. The mounting member and the wall portions of the applicator are generally made of plastic material. Especially the outer wall of the applicator is preferably made of material having a low heat conductivity (much lower than that of the porous member and contact member, so that the temperature of the applicator does not lower too much). At least part of the mounting member or receptacle may also be made in one piece with the heat exchanger. In other applications, especially those with moderately reduced temperatures, such as for treating swellings, the outer surface of the contact member will be much larger to contact a larger surface of the skin. Thus, the shape of the outer surface of the contact member will be varied in accordance with the disorder to be treated. In case of an applicator for treating piles in the anus, the applicator will have a narrower elongated part containing the contact member so that it can be inserted in the anus and the contact member surface will (also) be on the circumference of the elongated part, not (only) at the end thereof. The contact member surface may be covered by a thin layer of plastic. In other applications, especially for cosmetic purposes or for treating bites, the contact member surface may be covered by a soft layer, for example from plastic, resin or gel. Temperature control may be effected by changing the thickness of the layer. Such applicator may be used in combination with a skin moisturizer, ointment or the like.

FIGS. 21-24 show such embodiment where applicator 4 can be used in combination with an ingredient, in particular active ingredient. In the embodiment shown, the active ingredient is accommodated in a porous member 26, such as foam disposable, that can be removably attached, for example clicked or screwed, to applicator 4. In the embodiment shown, applicator 4 is recessed in the surroundings of contact member 11 in order to accommodate porous member 26 in contact with contact member 11. Thus, here contact member 11 is exposed to the outside through porous member 26, and thus indirectly to the site to be treated. The porous member may be deformable to release the active ingredient by pressure, but also other ways of releasing the ingredient are conceivable. The material and shape of the porous member is generally soft and/or smooth, such that it feels pleasant to the skin. The ingredient will generally be fluid, in particular cream or paste like, and may be active or may be inactive, just to feel pleasant to the skin during massage or cooling of the skin. The porous member 26, i.e. the foam disposable contains sufficient ingredient for one or a few treatments. The applicator 4 cools porous member 26, for example to a temperature between 5 and 10° C., and the porous member is configured to cool and massage the skin while releasing the active ingredient, as is illustrated in FIG. 23. Of course it is also possible to release the active ingredient first and then massage and cool the skin with the released ingredient. This method may be used, for example, for treating burns and stings, eye wrinkles, tired eyes, eczema or other skin irritation, nail and/or foot fungus, headache, swollen lips, sunburn in the face, is may be used on the feet by foot massage, it may be used during pregnancy and the like.

FIG. 24 shows porous member 4 packed in a package 27, such as a plastic foil or another packaging, so that the active ingredient is protected from the environment before use.

It is also conceivable to provide a porous member that is not attached to the applicator, but can be brought into contact with contact member 11 of applicator 4 in order to be cooled. The porous member may then be released an used separately.

This combination of cooling and application of active ingredients also enables the development and use of active ingredients that have improved functionality and/or are more active at lower temperatures Generally, the applicator and the container will be a disposable unit. However, especially with the embodiment in which the applicator is removable from the container, it is possible to have a reusable applicator sold separately, so that if the container is empty it can be replaced by a new one to which the old applicator is mounted. Therefore the invention also covers an applicator without the container, which is adapted to be mounted to a fitting container. The valve for supplying refrigerant may also be present in the applicator.

The invention claimed is:

1. A device for non-surgical cold treatment of disorders, comprising:
    a container containing a refrigerant and having an outlet for the refrigerant and a valve communicating with the outlet, wherein the valve is actuated by pressing,
    an applicator mounted or mountable to the container, said applicator having an outer wall and forming a chamber at least when connected to the container,
    a heat exchanger within the chamber in fluid communication with the outlet of the container and receiving refrigerant when the valve of the container is opened, and
    a closed contact member in heat exchange contact with the heat exchanger and being exposed to an outer side of the applicator,
    wherein the heat exchanger comprises a porous member made of a material having a high thermal conductivity and configured to conduct fluid refrigerant from the outlet of the container to the chamber while the refrigerant extracts heat from the heat exchanger and the contact member;
    wherein the valve is configured to maintain flow of the refrigerant to the heat exchanger and an amount of refrigerant delivered to the heat exchanger based by a duration of actuation of the valve by pressing; and
    wherein at least a portion of the porous member is within a receptacle that is positioned within the chamber, spaced from the outer wall of the applicator and open or vented to the chamber, the receptacle configured to receive refrigerant from the porous member.

2. The device of claim 1, wherein the porous member is made of a sintered material or plastic.

3. The device of claim 1, wherein the porous member is at least partly surrounded by a receptacle to receive any liquid refrigerant from the porous member therein, the receptacle being open to or vented to the chamber.

4. The device of claim 3, wherein the receptacle and the porous member form a narrow space between them.

5. The device of claim 3, wherein the receptacle is directly attached to the applicator.

6. The device of claim 1, wherein the applicator connects to the container so as to hold fluid therein but to allow gas to escape.

7. The device of claim 1, wherein the applicator, while attached to the container, is at least slidable in an axial direction with respect to the container between a depressed position that opens the valve, and a resting position, in which the valve is closed.

8. The device of claim 1, and further comprising a cover for the applicator covering the contact member.

9. The device of claim 1, wherein the contact member protrudes through the outer wall of the applicator and the heat exchanger fixed thereto is sealed with respect to the outer wall at an inner surface thereof.

10. The device of claim 1, wherein the applicator is removable from the container, the applicator having a substantially cylindrical sleeve portion which is slidably guided on an outer surface of the container.

11. The device of claim 10, wherein a substantially cylindrical contact member protrudes through the outer wall of the applicator.

12. The device of claim 11, wherein the outer wall of the applicator has substantially a shape of a dome concentrically around the contact member.

13. The device of claim 7, wherein the applicator has a member in contact with the outlet of the container which is surrounded by a collar, and an axial movement of the member causes axial depression of the outlet of the container to open the valve thereof, the device further comprising:
    a child-proof lock being positioned within the outer wall of the applicator and including at least one locking member which is movable between a locking position axially in line with the collar of the container to prevent axial movement of the applicator relative to the container and maintain the applicator in the resting position when the applicator is pressed in the axial direction by a user, and an unlocking position in which the locking member is displaced away from the locking position to allow axial movement of the applicator relative to the container to the depressed position when the applicator is pressed in the axial direction by a user,
    a holding member being connected to the at least one locking member to convert a non-axial movement of the outer wall into a movement of the at least one locking member from the locking position to the unlocking position.

14. A device for non-surgical cold treatment of disorders, comprising:

a container containing a refrigerant and having an outlet for the refrigerant and a valve communicating with the outlet, wherein the valve is actuated by pressing, an applicator mounted to the container, said applicator having an outer wall and forming a chamber at least when connected to the container, a heat exchanger within the chamber in fluid communication with the outlet of the container and receiving refrigerant when the valve of the container is opened during actuation of the valve by pressing, and a closed contact member in heat exchange contact with the heat exchanger and extending through the outer wall of the applicator, wherein the closed contact member includes a contact member surface that is exposed to an outer side of the applicator, a material of the heat exchanger and shape of the contact member surface is chosen in dependence of the disorder to be treated, wherein the applicator, while attached to the container, is at least slidable in an axial direction with respect to the container between a depressed position that opens the valve, and a resting position, in which the valve is closed.

15. A device for release of a substance from a container having an outlet for the substance and a valve communicating with the outlet which is surrounded by a collar, comprising:

an applicator mounted to the container, said applicator having an outer wall and a member in contact with the outlet of the container, wherein the applicator, while attached to the container, is movable with respect to the container in an axial direction of the collar between a depressed position, in which the outlet of the container is axially depressed by the applicator to open the valve of the container, and a resting position, in which the valve is closed, a child-proof lock being positioned within the outer wall of the applicator and including at least one locking member which is movable between a locking position axially in line with the collar of the container to prevent axial movement of the applicator relative to the container and maintain the applicator in the resting position when the applicator is pressed in the axial direction by a user, and an unlocking position in which it is displaced away from the collar allowing axial movement of the applicator relative to the container to the depressed position when the applicator is pressed in the axial direction by a user, a holding member being connected to the at least one locking member to convert a non-axial movement of the outer wall into a movement of the at least one locking member from the locking position to the unlocking position.

16. The device of claim 15, wherein the holding member is a flexible arm pulling the locking member from the locking position to the unlocking position.

17. The device of claim 15, wherein the at least one locking member is a cam.

18. The device of claim 15, wherein the applicator is mounted to the container by a sleeve portion, the outer wall of the applicator being rotatable with respect to the sleeve portion around an axis of the collar.

19. The device of claim 18, wherein the locking member, when in its locking position, rests in a seat formed on an inner side of a wall portion, the seat being provided with a seat wall portion urging the locking member inwardly when the seat is moved by the outer wall rotating with respect to the sleeve portion, the holding member holding the locking member in a circumferential direction.

20. The device of claim 1, wherein the porous member is contactable with the contact member of the applicator.

21. The device of claim 20, wherein the porous member is attachable to the applicator in contact with the contact member.

22. The device according to claim 20, wherein the porous member comprises foam.

23. A method of operating a device for cold treatment of disorders, the method comprising:

providing a device comprising:
a container containing a refrigerant and having an outlet for the refrigerant and a valve communicating with the outlet, wherein the valve is actuated by pressing;

an applicator mounted or mountable to the container, said applicator having an outer wall and forming a chamber at least when connected to the container;

a heat exchanger within the chamber in fluid communication with the outlet of the container and receiving refrigerant when the valve of the container is opened, the heat exchanger including a porous member formed of a material having a high thermal conductivity, the porous member is at least partially received within a receptacle that is positioned within the chamber, spaced from the outer wall of the applicator and open or vented to the chamber, the receptacle configured to receive refrigerant from the porous member; and a closed contact member in heat exchange contact with the heat exchanger and being exposed to an outer side of the applicator;

wherein the valve is configured to maintain flow of the refrigerant to the heat exchanger and an amount of refrigerant delivered to the heat exchanger based by a duration of actuation of the valve by pressing;

depressing the applicator to actuate the valve through the applicator;

discharging the refrigerant from the container in response to depressing the applicator;

extracting heat from the contact member and the porous member using the discharged refrigerant; and applying the contact member of the applicator to the disorder.

* * * * *